United States Patent [19]

Natale

[11] 4,336,029
[45] Jun. 22, 1982

[54] METHOD AND REAGENTS FOR QUANTITATIVE DETERMINATION OF RETICULOCYTES AND PLATELETS IN WHOLE BLOOD

[75] Inventor: Peter J. Natale, Canton, Mass.

[73] Assignee: Ortho Diagnostic Systems Inc., Raritan, N.J.

[21] Appl. No.: 178,481

[22] Filed: Aug. 15, 1980

[51] Int. Cl.³ .................... G01N 21/64; G01N 33/52
[52] U.S. Cl. .................... 23/230 B; 250/461 B; 252/408
[58] Field of Search .................... 250/461 B; 424/3; 356/39; 252/408; 23/230 B

[56] References Cited

U.S. PATENT DOCUMENTS

| | | | |
|---|---|---|---|
| 3,497,690 | 2/1970 | Wheeless, Jr. et al. | 250/461 B |
| 3,684,377 | 8/1972 | Adams et al. | 250/461 B X |
| 3,864,571 | 2/1975 | Stillman et al. | 250/461 B |
| 3,883,247 | 5/1975 | Adams | 250/461 B |
| 3,916,205 | 10/1975 | Kleinerman | 250/461 B |
| 3,997,656 | 12/1976 | Wertlake et al. | 424/3 |
| 4,027,971 | 6/1977 | Kolman et al. | 356/39 X |
| 4,146,604 | 3/1979 | Kleinerman | 252/408 X |

Primary Examiner—Arnold Turk
Attorney, Agent, or Firm—Geoffrey G. Dellenbaugh; Mark A. Hofer

[57] ABSTRACT

Methods and compositions for quantitating reticulocytes and platelets by fluorescence in a flow cytometer. The composition comprises an aqueous solution of the dye acridine orange, citrate ion, and para-formaldehyde at a pH of about 7.4 and an isotonic osmolality. The concentrations of the various ingredients are selected to maximized dye uptake by the reticulocytes and platelets to allow for the first time the fluorescent quantitation of these cells in whole blood using a flow cytometer.

4 Claims, 4 Drawing Figures

METHOD AND REAGENTS FOR QUANTITATIVE DETERMINATION OF RETICULOCYTES AND PLATELETS IN WHOLE BLOOD

BACKGROUND OF THE INVENTION

1. Field of the Invention

The present invention relates to methods and reagents for enumerating cells in samples of whole blood, and more particularly to methods and reagents for quantitatively determining reticulocyte and/or platelet levels in a whole blood specimen by fluorescence using a flow cytometer.

2. Description of the Prior Art

Blood is a fluid, circulating tissue found in all higher animals and in many invertebrates. It is a tissue, just as skin, muscle, and bone are tissue, because it contains living cells and has specific functions, chief among which being the conveyance of materials from one part of the body to another. The general principal on which the chemical life of an organism is conducted is that each living cell carries out within itself all the chemical processes necessary to its existence. Therefore, all of the materials required by each cell must be carried to it and all of the wastes must be removed. Throughout the bodies of higher animals, a highly specialized system of transport, called the blood vascular system, has evolved which affords an efficient route for the blood and provides the necessary intimate contact thereof with every living cell.

The principal materials which a living cell requires are sugar, amino acids, fats, vitamins, oxygen, salts, hormones, and water. The organs of digestion convert the solid constituents of food into forms that the blood can absorb and deliver to the cells of the body. The principal wastes which must be removed are carbonic acid and simple soluble compounds of nitrogen.

In all the higher animals, blood consists of an aqueous fluid part (the plasma) in which are suspended corpuscles of various kinds: the red blood cells (erythrocytes), the white blood cells (leukocytes), and the blood platelets. Plasma has a composition comprising roughly 90% water, 9% protein, 0.9% salts, and traces of other materials such as sugar, urea, uric acid, and the like. Plasma, in fact, resembles nothing so much as the primordial ocean in which the first unicellular animals developed.

The concentration of salts in plasma is important principally to assist dissolution of proteins. Most proteins will not dissolve in pure water and are therefore essentially unusable by living material without salts.

The normal concentration of hydrogen ions in plasma is $0.4 \times 10^{-7}$ grams of hydrogen per liter, for a pH of 7.4. Because of the adverse affects of substantial variation from this level, the body acts to maintain the blood pH at 7.4.

The cells or corpuscles of the peripheral blood (i.e., the blood outside the bone marrow) are divided into two main groups: the red blood cells (erythrocytes), whose primary object is to transport oxygen, and the white blood cells (leukocytes), whose primary functions relate to the immune system and the destruction of materials foreign to the body. In addition to these two main groups, the blood also contains the so-called blood platelets, which are important in hemostasis.

The final stages of erythrocyte maturation occur after their release from the bone marrow while these cells are circulating in the peripheral blood. These young red cells, or "reticulocytes" have lost their nucleus and thus their ability to divide or to synthesize RNA. Although these functions have ceased, reticulocytes are still metabolically active and are capable of synthesizing protein, taking up iron for the synthesis of heme, and carrying out the necessary metabolic reactions required to maintain an energy rich state. These cells are usually distinguished from mature erythrocytes through the presence of the reticulum, which give them their name. This reticulum may be dyed by such agents as brilliant cresyl blue, nile blue sulfate, or new methylene blue, after which quantitation of reticulocytes may be performed by way of manual observation under a microscope.

Although reticulocytes normally comprise about one percent of the total red blood cell population, this percentage can change dramatically under abnormal conditions. For example, reticulocyte counts have been used for many years as a diagnostic aid in studying blood dyscrasias and as an index of red cell regeneration following hemorrhage, as well as for monitoring early toxicity in chemotherapy of certain malignant diseases.

Blood platelets are also produced in the bone marrow and are important in hemostasis, both in the formation of the primary hemostatic plug and in the intrinsic coagulation mechanism. Platelets are usually from one to four microns in diameter and circulate in the blood as smooth, disc-shaped cells having a circulating life span of approximately nine to eleven days. The measurement of platelet concentration is an important diagnostic aid in studying disorders of the blood coagulation system.

The enumeration of platelets is usually performed at the present time either by manual phase contrast microscopy or by automated systems based on electroconductometric or optical light scatter measurements. However, each of these techniques has its own disadvantages. With the manual phase contrast microscope, counting becomes extremely tedious, which could of course have significant effects on both accuracy and precision. Any manual counting technique places severe limits on the size of the population of cells which can be counted. Moreover, the smaller platelets are often masked by the larger red blood cells. An underlying problem with either of the automated methods is the inability to obtain conditions having a high signal to noise ratio. Thus, it is difficult to obtain sufficiently accurate measurements apart from background. Moreover, these measurements have an inherent inability to distinguish giant platelets from small erythrocytes. Other problems are presented by the currently-used automatic apparatus, such as clogging with the electroconductometric apparatus and the requirement of especially pure reagents to minimize microscopic debris for optical scatter apparatus.

The use of fluorescing stains or dyes for analysis of blood cells has been known for many years. For example, J. B. Vander, et al., J. Lab. Clin. Med 62, 132 (1963) described the use of the dye acridine orange for the identification of reticulocytes by fluorescent microscopy. However, this technique still requires visual examination of the sample and thus possesses the inherent disadvantages of such manual optical examination methods.

Additionally, many different types of automatic apparatus have been disclosed for detecting and quantitating blood cells, particularly white blood cells. Representative of such methods (some of which use acridine orange or other fluorescent dyes) are U.S. Pat. Nos. 3,497,690; 3,916,205; 3,864,571; and 4,027,971. While these references generally disclose the use of fluorescent dyes in a variety of apparatus, including a flow cytometer, they still fail to solve the problems of the prior art and do not provide a method or composition for quantitating reticulocytes or platelets by fluorescence.

Of particular interest in this regard are U.S. Pat. Nos. 3,684,377 (Adams and Kamentsky) and 3,883,247 (Adams). These patents relate to methods and dye compositions for quantitating cells (particularly white blood cells) using a metachromatic fluorochrome dye such as acridine orange.

The Adams and Kamentsky '377 patent describes the use of a vital dye composition for differential blood analysis of living white cells which consist essentially of acridine orange having a concentration between $10^{-7}$ and $10^{-5}$ grams per liter, the acridine orange solution having a pH factor and an osmolality within the normal physiological ranges for human blood plasma. While this '377 patent teaches that this composition is useful for identifying the various types of white blood cells and for distinguishing them from other bodies in the blood, there is no teaching that this composition has any use in the enumeration of reticulocytes or platelets.

The Adams '247 patent represents a modification of the teaching of the Adams and Kamentsky '377 patent in that the white blood cells are treated under conditions in which the cells are "shocked" by exposure to a non-physiologic medium during staining. That is, the staining composition used in the Adams '247 patent is made hypotonic, the osmolality or salinity thereof being generally below that normally found in human blood. The teaching of the Adams '247 patent is that this hypotonic condition produces a differential rate of uptake of acridine orange dye by the various types of white blood cells, thus allowing them to be more clearly distinguished from one another than in previous techniques. However, as with the Adams and Kamentsky '377 patent, the Adams '247 patent does not teach the quantitation of platelets. Moreover, although the Adams '247 patent does purport to disclose a method for the detection of reticulocytes, the method disclosed has been found by the present applicant to be practically useless for the quantitation of either reticulocytes or platelets, as further described below.

Accordingly, there exists a need for methods and reagents useful for quantitating reticulocytes and platelets by fluorescense using a flow cytometer. It is a principal object of the present invention to provide such reagent and methods.

SUMMARY OF THE INVENTION

The present invention provides for the first time dye compositions and methods which can quantitate reticulocytes and platelets in a whole blood sample by fluorescence using a flow cytometer.

The dye composition of the present invention consists essentially of an aqueous solution of the metachromatic fluorochrome dye acridine orange, a chelating agent, an amino-group reacting reagent, and (if needed) a buffer to maintain the final pH of this solution at approximately 7.4. The osmolality of the solution is maintained at approximately 0.26 osmolality units, the normal physiological level, either by the chelating agent or by addition of sodium chloride as required.

One dye composition which has been found to be particularly effective consists essentially of an aqueous solution of acridine orange at a concentration of about 0.01 grams per liter, citric acid at about 13.66 grams per liter, para-formaldehyde at about 2.0 grams per liter, and sufficient sodium hydroxide to bring the final pH of the solution to about 7.4. In this preferred reagent, the citric acid acts as the chelating agent and is also present in a sufficient amount to make the resulting solution isotonic (that is, having a physiological level of osmolality). The para-formaldehyde acts as the amino-reacting reagent. Since citric acid/sodium citrate is an effective buffer at pH 7.4, no additional buffer is required. This dye composition may be successfully used in a blue laser flow cytometer to quantitate reticulocytes and platelets.

In contrast to the Adams and Kamentsky '377 patent and the Adams '247 patent, in which the differentiation of the subtypes of white blood cells depends upon the rate of uptake of the acridine orange dye, the present invention depends upon removing the kinetic factors and increasing the degree of dye uptake so that the reticulocytes and platelets will absorb a maximum amount of acridine orange dye. Only if this maximum amount is absorbed will the problems of prior art reagents and methods be overcome. With prior art staining reagents, the platelets and reticulocytes absorb only small amounts of dye and therefore yield only low levels of fluorescence in any fluorescence detecting method. These low levels of fluorescence could generally not be well detected over the background fluorescence and consequently only a portion of reticulocytes or platelets could be detected.

It will therefore be understood that the concentration of acridine orange dye in the subject dye composition must be enough to fully stain the reticulocytes and platelets, while not being so much as to stain with non-specific protein in (e.g.) the red blood cells. This concentration of acridine orange dye, sometimes referred to herein as an "effective reticulocyte and platelet quantitating concentration," can readily be determined by those skilled in the art. As a preferred range, the concentration may be 0.01 grams per liter plus or minus about 20%.

One preferred chelating reagent is the citrate ion, although other effective magnesium ion chelating agents such as EGTA [ethyleneglycol-bis-($\beta$-aminoethylether)-N,N'-tetraacetic acid] or the like could be used. In the preferred dye composition disclosed above, the citrate ion is added as citric acid in order that it may simultaneously act as a buffer in the presence of sodium hydroxide. However it is within the scope of the present invention to use other well-known buffers if required. The amount of chelating reagent in the dye composition should be selected to effectively chelate magnesium ion to maximize the acridine orange uptake by the platelets and reticulocytes. The concentration of citrate ion may vary from about 10.5 grams per liter citric acid (0.055 M) to about 14 grams per liter citric acid (0.073 M) any decrease in osmolality being compensated for by addition of an appropriate concentration of sodium chloride.

The amino-reacting reagent may be an aldehyde, such as glutaraldehyde, formaldehyde, or para-formaldehyde, or other amino-reacting groups such as ketene, and the like. It has been found that para-formaldehyde is particularly useful. The amount of amino-reacting reagent should be selected to maximize the number of dye-reacting sites and promote maximum acridine orange uptake by the reticulocytes and platelets. The amount of para-formaldehyde may vary from about 1.0 grams per liter to about 3.0 grams per liter, but about 2 grams per liter is preferred because it enhances the storage stability of the subject dye composition.

It should be emphasized that the prior art disclosures regarding acridine orange specifically taught against having maximum acridine orange uptake, since such maximum uptake would destroy the discrimination among the various subclasses of white blood cells which was the main object of these prior art methods. Therefore, the prior art Adams and Adams and Kamentsky patents cannot be said to teach the subject composition or method.

The subject dye composition may be used to enumerate reticulocytes and platelets in a whole blood specimen using the technique of flow cytometry.

The fundamental concept of flow cytometry is essentially the passing of cells, one at a time, through a specific sensing region. By means of hydrodynamic focusing, single cells are passed through the sensing zone, which consists of a focused lasar light source and a detection system for the measurement of scattered and fluorescent light. Commercially available flow cytometers having a blue laser, such as the FC200-4800A CYTOFLUOROGRAF*, sold by the assignee of the present application, are suitable for such measurements. As used herein the term "blue laser" means an argon ion laser emitting light at a wavelength of 4880 Angstrom units (488 millimicrons). When excited by such a blue laser, platelets and reticulocytes stained by the subject dye composition produce red fluorescence at about 6500 Angstrom units due, it is believed, to the stacking of dye molecules on the RNA contained therein.

Accordingly, the subject method in its broadest application comprises the steps of:
(a) mixing a sample of blood to be tested with the subject dye composition to form a suspension;
(b) allowing the suspension to react for a sufficient time so that the acridine orange dye is maximally taken up by the reticulocytes and platelets;
(c) exposing the suspension to radiation from a blue laser light source; and
(d) measuring the intensity of red fluorescence and amount of narrow forward scattered light from the suspension; and
(e) determining the amount or percentage of reticulocytes or platelets in the sample from said measurements.

DETAILED DESCRIPTION OF THE INVENTION

Figure 1:
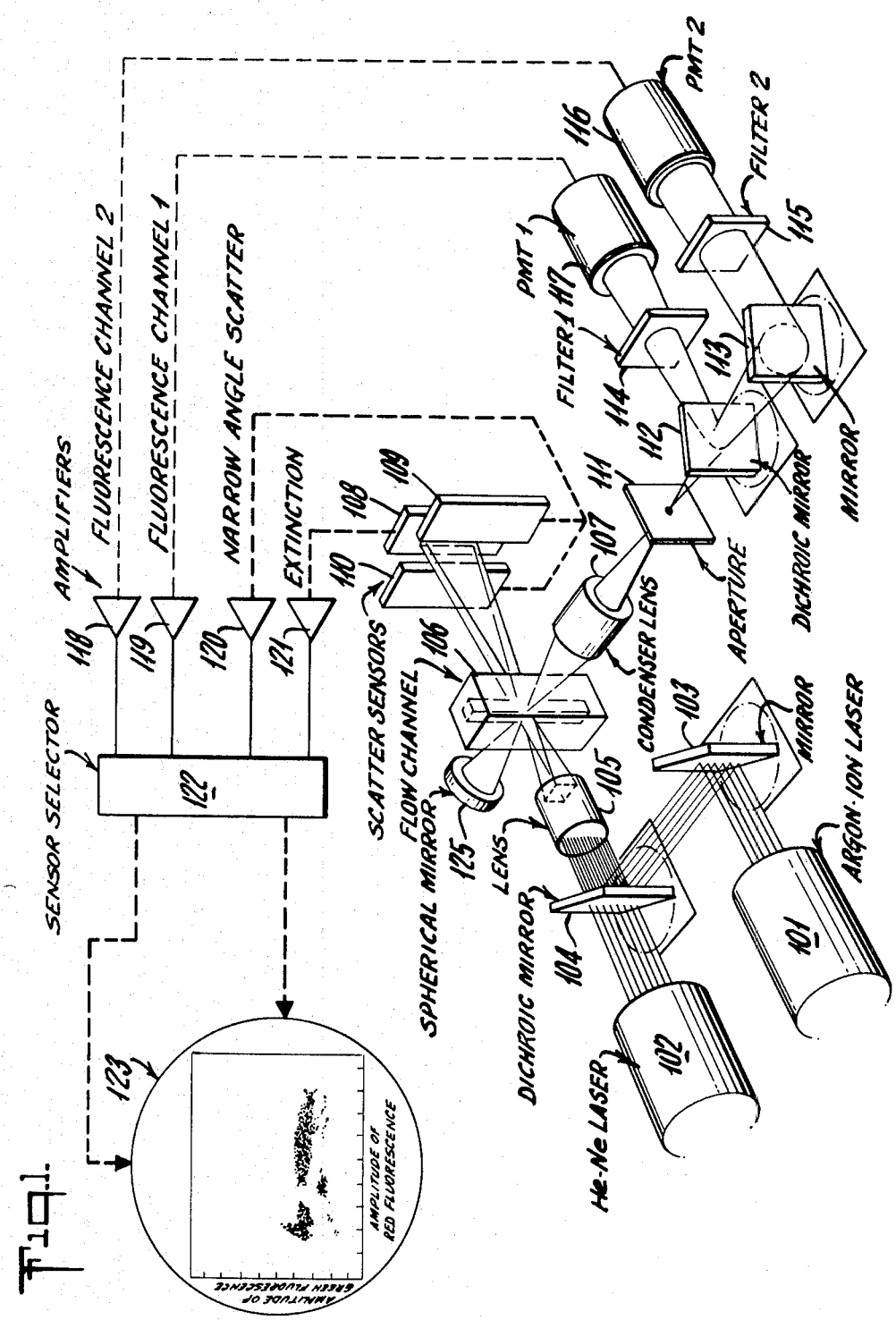
FIG. 1 shows a stylized version of a commercially-available flow cytometric system, which is suitable for use in the practice of the present invention.
Figure 2:
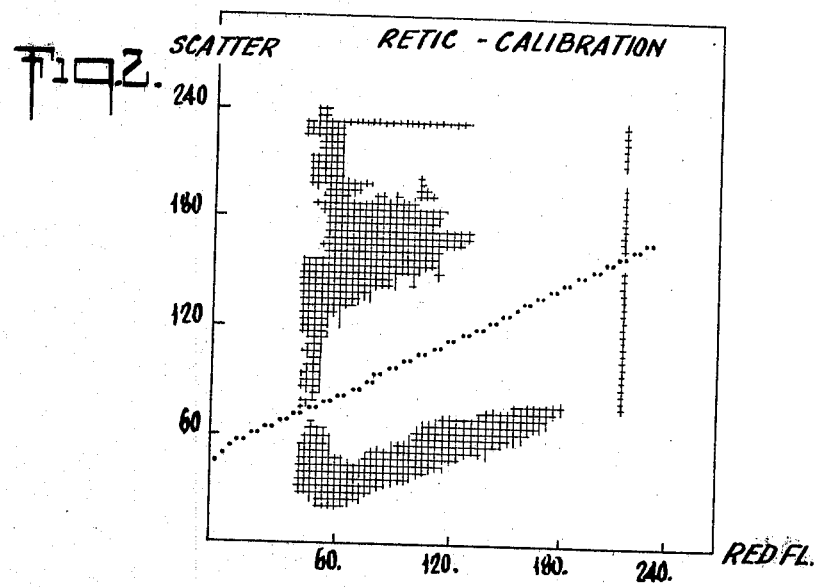
FIG. 2 shows a typical histogram produced according to the present invention.

Referring first to FIG. 1, there is shown a stylized functional and structural representation of apparatus which may be utilized in accordance with the principles of the present invention. In fact, the apparatus of FIG. 1 depicts a particular system available commercially under the trade designation CYTOFLUOROGRAPH*, which is sold by the assignee hereof. The apparatus of FIG. 1 incorporates the principles of flow cytometry for cell analysis, and includes capacity for sensing fluorescent response of cells to specific types of illumination.

Focal to the FIG. 1 apparatus is a flow channel 106, wherein cells in liquid suspension are passed, in single file and at a rapid rate (e.g., 2500 cells per second) through a sensing zone. The sensing zone is defined by the intersection of cell flow and an incident light beam, typically focused coherent light from a gas laser. As the cell passes through the sensing zone, it interacts with incident light in a variety of ways. Some light, of course, is absorbed by the cell, other light is scattered at relatively narrow angles to the axis of incident light, and still other light is scattered at angles quite divergent from the axis of incident light, for example at right angles to the incident light. Furthermore, depending upon the nature of the cell itself, and any dyeing or staining to which the cell may previously have been subjected, fluorescence emissions may occur.

Accordingly, photosensors located at various orientations with respect to the cell stream and the incident laser light permit detection of a unique set of responses for each given type of cell. Thus FIG. 1 includes an argon ion laser 101 and a helium neon laser 102, with the coherent light emitted by each being variously deflected via mirrors 103 and 104 and a lens 105 to the sensing zone of the flow channel 106. As is known in the art, the cell sample stream is carried in laminar fashion within a flowing fluid sheath, to insure that but a single cell will be illuminated in the sensing zone at a given time. Hence, as each cell is illuminated by light from the lens, interaction of the cell with the light may be sensed.

As shown in FIG. 1, an extinction sensor 108 detects the amount of light blocked by the cell, and forward light scatter is detected by photosensors 109 and 110 approximately in a cone of half-angle 20°. Electrical signals generated by the sensors 108, 109 and 110 are coupled to amplifiers 120 and 121, which present electrical signals of suitable amplitude and the like for subsequent analysis and/or display.

In the apparatus of FIG. 1, light which is emitted from the cell by virtue of a fluorescence response is sensed at right angles both to the direction of cell flow and to the axis of incident light. A spherical mirror 125 and a condenser lens 107 collects this light approximately in a cone of half-angle 20°, and couples this light through an aperture 111, successively to a dichroic mirror 112 and to a second mirror 113. A first color filter 114 (e.g., to pass relatively long wavelength light) conveys select light from the dichroic mirror 112 to photosensor 117 (e.g., a photomultiplier tube). A second filter 115 selectively passes light of a different color (e.g., relatively short wavelength light) from the second mirror 113 to a second photosensor 116. Electrical signals from sensors 116 and 117, in the form of pulses corresponding to light from respective cells, are coupled to amplifiers 118 and 119, thereby also to produce signals which are adapted for suitable processing.

As shown in the FIG. 1 embodiment, a sensor selector 122 generates output histograms utilizing signals from the amplifiers 118 through 121. For example, one useful form of output is a plot of amplitude of red fluorescense, from sensor 117, against amplitude of green fluorescence, from sensor 116. Such a histogram is shown at display 123, with each point on the histogram representing an individual cell. Clusters or aggregates of indicators on the histogram represent groups of cells of similar type. Quite evidently, those of ordinary skill in the art find it useful variously to generate histograms of narrow forward angle scatter versus intensity of green fluorescence, narrow forward angle scatter versus axial light extinction, and so forth.

In the present invention, quantitation of reticulocytes and platelets is accomplished by generating a histogram of the amount narrow forward angle scatter versus intensity of red fluorescence. Reticulocytes and platelets will appear as separate dot groupings on this histogram. The percent or number of reticulocytes and platelets may then be determined by creating an electronic "window" defining ranges of narrow forward angle scatter and intensity of red fluorescence which identify reticulocytes or platelets, and determining the percent of the total cells which fall in this "window," thus yielding the percent or number of reticulocytes or platelets in the total cell population. This "window" technique is well-known in the art as shown, e.g., by Adams U.S. Pat. No. 3,883,247.

The dye acridine orange, which an important constituent of the subject dye composition is an organic compound for which the chemical name is 3,6-bis-(dimethylamino)-acridinium chloride. Acridine orange is also identified by color index specification 46,005 from the publication entitled COLOR INDEX, Second edition (1956, 1957), published jointly by the Society of Dyers and Colorists of Great Britain and by the American Association of Textile Chemists and Colorists. Acridine orange is commercially available, e.g., from Polyscience, Inc., Warrington, Pa.

In the subject dye compositions, the mixture of acridine orange and the other ingredients may not be a true solution, but may partly be a suspension of aggregates of dye molecules or (perhaps more properly) a colloidal dispersion in which extremely minute undissolved particles are suspended in the liquid. However, this composition is referred to as a "solution" throughout this specification to contrast it with the mixture of the acridine orange solution with a blood sample, which is referred to as a "suspension." Thus, while the acridine orange composition may not be a true solution, the use of that term serves to distinguish the dye composition per se from the liquid suspension formed after mixing with the blood sample.

The subject invention is illustrated by the following examples.

EXAMPLE I

A dye composition suitable for use in accordance with the present invention is produced having 0.01 grams per liter acridine orange, 13.66 grams per liter citric acid, 2.0 grams per liter para-formaldehyde, and sufficient sodium hydroxide to adjust the final pH of the solution to 7.40.

This composition can be produced by adding the other ingredients sequentially to water, followed by adjustment of the pH.

This dye composition was used in accordance with the teachings of this invention and was found to allow excellent quantitation of reticulocytes and platelets using a blue laser flow cytometer.

EXAMPLE II

For comparison with the prior art, a dye composition was prepared following Example XIV of Adams U.S. Pat. No. 3,883,247. In contrast to the material of Example I, this prior art composition did not allow quantitation of reticulocytes or platelets in a blue laser flow cytometer. In fact, only about 50% of reticulocytes and platelets in a group of blood samples of known composition were detected using this prior art dye composition.

EXAMPLE III

Figure 3:
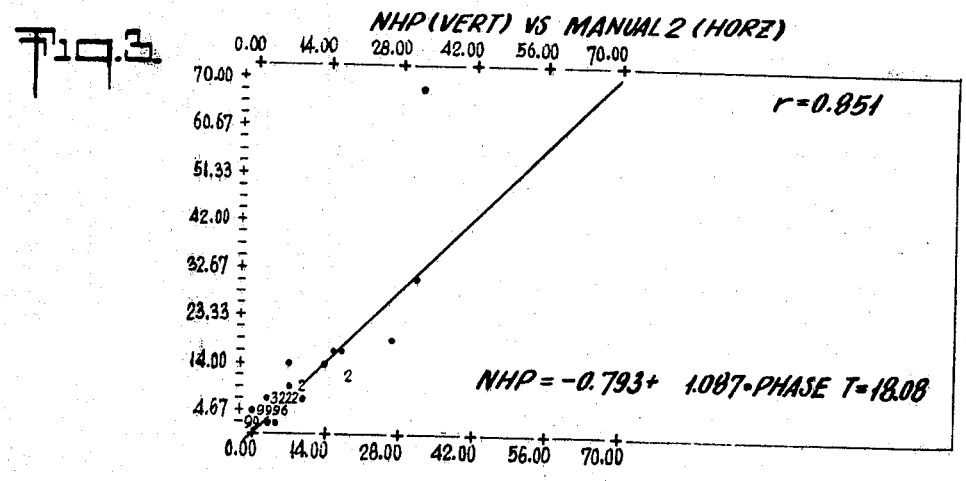
FIG. 3 shows a correlation diagram comprising percent reticulocytes measured according to the present invention with that measured using a prior art microscopic technique.

A comparative trial was conducted to compare percent reticulocytes obtained according to the present invention with that obtained using a prior art microscopic technique. A population of 126 samples of EDTA-treated whole blood was evaluated by both techniques and the results plotted on a correlation diagram shown in FIG. 3. The correlation was excellent.

According to the present invention, a portion of each sample was combined with the reagent of Example I and allowed to react for 2–5 minutes. The resulting suspension was flowed through a flow cytometer equipped with a blue laser, narrow forward light scatter and red fluorescence were measured, and the percent reticulocytes was calculated.

For comparison with the prior art, a second portion of each sample was stained with new methylene blue and manually counted under a microscope.

EXAMPLE IV

Figure 4:
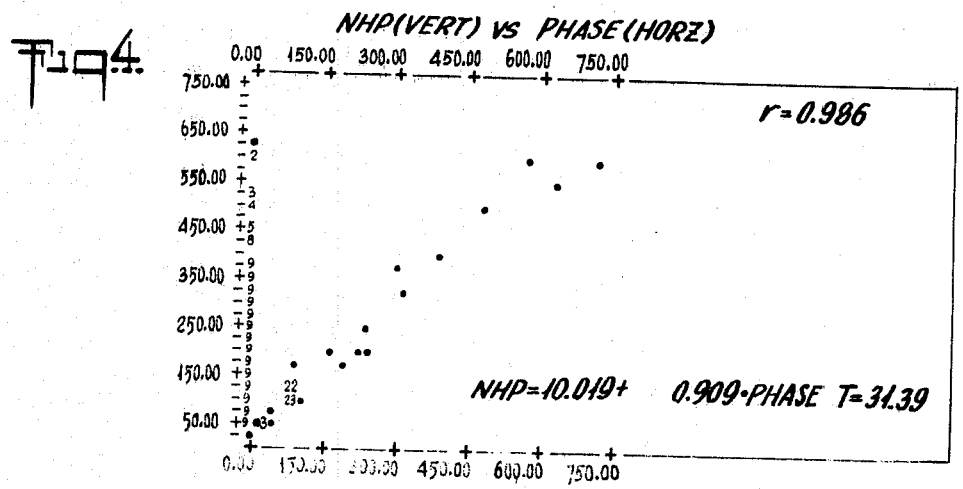
FIG. 4 shows a correlation diagram comparing percent platelets measured according to the present invention with that measured by various prior art techniques.

A further comparative trial as in Example III was conducted to compare amount of platelets obtained according to the present invention with that obtained using a prior art technique. A population of 30 samples of EDTA-treated whole blood was evaluated by both techniques and the results plotted on a correlation diagram shown in FIG. 4. The correlation was excellent.

According to the present invention, a portion of each sample was combined with the reagent of Example I and allowed to react for 2–5 minutes. The resulting suspension was flowed through a flow cytometer equipped with a blue laser, narrow forward light scatter and red fluorescence were measured, and the amount of platelets was calculated.

For comparison with the prior art, a second portion of each sample was manually counted using phase contrast microscopy.

What is claimed is:

1. A dye composition for quantitation of reticulocytes and platelets in a whole blood sample by fluorescence using flow cytometry which consists essentially of an aqueous solution of an effective reticulocyte and platelet quantitating concentration of acridine orange dye, an effective magnesium ion chelating amount of citrate ion, and an effective maximum acridine uptake promoting concentration of an amino-reacting reagent; the aqueous solution having a pH of from about 7.3 to about 7.5 and having a physiological level of osmolality.

2. A dye composition useful for quantitating reticulocytes and platelets in a whole blood sample by fluorescence using flow cytometry which consists essentially of an aqueous solution of from about 0.008 grams per liter to about 0.012 grams per liter of acridine orange, from about 10.5 grams per liter to about 14 grams per liter of citric acid, from about 1.0 gram per liter to about 3.0 grams per liter of para-formaldehyde, and sufficient sodium hydroxide to bring the final pH of the solution to from 7.30 to 7.50.

3. A method for quantitating reticulocytes or platelets in a whole blood sample by flow cytometry which comprises the steps of:

(a) mixing a sample of blood to be tested with the reagent of claim 1 to form a suspension;
(b) allowing the suspension to react for a sufficient time so that the acridine orange dye is maximally taken up by the reticulocytes and platelets;
(c) exposing the suspension to radiation from a blue laser light source;
(d) measuring the intensity of red fluorescence and amount of narrow forward scattered light from the suspension; and
(e) determining the amount or percentage of reticulocytes or platelets in the sample from said measurements.

4. A method for quantitating reticulocytes or platelets in a whole blood sample by flow cytometry which comprises the steps of:
(a) mixing a sample of blood to be tested with the reagent of claim 2 to form a suspension;
(b) allowing the suspension to react for a sufficient time so that the acridine orange dye is maximally taken up by the reticulocytes and platelets;
(c) exposing the suspension to radiation from a blue laser light source;
(d) measuring the intensity of red fluorescence and amount of narrow forward scattered light from the suspension; and
(e) determining the amount or percentage of reticulocytes or platelets in the sample from said measurements.

* * * * *